(12) United States Patent
Niu et al.

(10) Patent No.: US 7,781,200 B2
(45) Date of Patent: Aug. 24, 2010

(54) POLYPEPTIDES HAVING LIPASE ACTIVITY AND POLYNUCLEOTIDES ENCODING SAME

(75) Inventors: Xiao Mei Niu, Beijing (CN); Ye Liu, Beijing (CN); Jurgen Carsten Franz Knotzel, Copenhagen Ø (DK); Signe Munk, Charlottenlund (DK)

(73) Assignee: Novozymes A/S, Bagsvaerd (DK)

( * ) Notice: Subject to any disclaimer, the term of this patent is extended or adjusted under 35 U.S.C. 154(b) by 309 days.

(21) Appl. No.: 11/774,276

(22) Filed: Jul. 6, 2007

(65) Prior Publication Data

US 2008/0020118 A1    Jan. 24, 2008

Related U.S. Application Data

(60) Provisional application No. 60/834,997, filed on Aug. 2, 2006.

(30) Foreign Application Priority Data

Jul. 14, 2006    (DK) ............................... 2006 00980

(51) Int. Cl.
   *C12N 9/20*     (2006.01)
   *A61K 38/46*    (2006.01)
   *C12P 21/02*    (2006.01)
   *C07K 14/37*    (2006.01)

(52) U.S. Cl. ..................... 435/198; 424/94.6; 435/69.1; 530/350

(58) Field of Classification Search ............ 435/198, 435/69.1; 424/94.6; 530/350
   See application file for complete search history.

(56) References Cited

U.S. PATENT DOCUMENTS 6,103,505 A * 8/2000 Clausen et al. ............ 435/134

FOREIGN PATENT DOCUMENTS

| EP | 0 258 068 | 2/1988 |
|----|-----------|--------|
| EP | 0 305 216 | 1/1989 |
| WO | WO 92/05249 | 4/1992 |
| WO | WO 94/25577 | 11/1994 |
| WO | WO 95/22615 | 8/1995 |
| WO | WO 97/04079 | 2/1997 |
| WO | WO 97/07202 | 2/1997 |
| WO | WO 02/00852 | 1/2002 |
| WO | WO 02/066622 | 8/2002 |
| WO | WO 2005/087918 | 9/2005 |
| WO | WO 2008/010920 | 1/2008 |

OTHER PUBLICATIONS

Meinkoth and Wahl, Current Protocols in Molecular Biology, Hybridization Analysis of DNA Blots, Chap. 2, pp. 2.10.8-2.10.11, 2000.*
Alignment of SEQ ID No. 2 with SEQ ID No. 2 of Clausen et al., US 6,103,505, Result 1 from a search in the issued patents polypeptide database, .rai, performed on Jun. 26, 2009.*
Blast2, mature polypeptide coding region of SEQ ID No. 1 vs. SEQ ID No. 1 of Clausen et al., US 6,103,505, performed on the NCBI website, http://blast.ncbi.nlm.nih.gov/Blast.cgi, on Jul. 17, 2009.*
Eddine et al., Mol. Genetic Genomics, vol. 265, pp. 215-224 (2001).

* cited by examiner

*Primary Examiner*—Karen Cochrane Carlson
*Assistant Examiner*—Rosanne Kosson
(74) *Attorney, Agent, or Firm*—Kristin J. McNamara

(57) ABSTRACT

The present invention relates to a new wild-type lipase, its nucleic acid sequences and the amino acid sequences thereof. This new lipase shows washing performance in the form of wild-type. The present invention also relates to the method for producing the lipase and the uses of the lipase in baking.

15 Claims, No Drawings

POLYPEPTIDES HAVING LIPASE ACTIVITY AND POLYNUCLEOTIDES ENCODING SAME

CROSS-REFERENCE TO RELATED APPLICATIONS

This application claims priority or the benefit under 35 U.S.C. 119 of Danish application no. PA 2006 00980 filed Jul. 14, 2006 and U.S. provisional application No. 60/834,997 filed Aug. 2, 2006, the contents of which are fully incorporated herein by reference.

REFERENCE TO SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material which has been made at Deutsche Sammlung von Mikroorganismen und Zelikulturen GmbH (DSM) under the Budapest Treaty on 21 Jul. 2005 and assigned accession number DSM 17467 which microbial deposit(s) is incorporated herein by reference.

FIELD OF THE INVENTION

The present invention relates to isolated polypeptides having lipase activity and isolated polynucleotides encoding the polypeptides. The invention also relates to nucleic acid constructs, vectors, and host cells comprising the polynucleotides as well as methods for producing and using the polypeptides.

BACKGROUND OF THE INVENTION

For a number of years, lipases have been used as detergent enzymes to remove lipid or fatty stains from clothes and other textiles (EP 258 068 and EP 305 216). Patent publications WO 92/05249, WO 94/25577 WO 95/22615, WO 97/04079 and WO 97/07202 disclose variants of the *H. lanuginosa* lipase having improved properties for detergent purposes. Thus, WO 97/04079 discloses variants having a peptide addition (extension) at the N-terminal and/or the C-terminal. VAK 97107202 discloses lipase variants with "first wash performance" which are capable of removing substantial amounts of lard from a lard stained swatch in a one-cycle wash.

However, there is an ever existing need for providing novel lipases with improved washing properties in a variety of commercial detergents. The present invention relates to such novel lipases.

Thus, it is an object of the present invention to provide polypeptides having lipase activity and polynucleotides encoding the polypeptides. This new lipase shows performance similar to a known lipase (SEQ ID NO: 12) at pH 9 in the absence of detergent, and shows washing performance in the form of a wild-type.

SUMMARY OF THE INVENTION

The inventors have found a new wild-type lipase originally from fungal species *Nectria* sp. The subjected new wild-type lipase shows performance similar to a well-known lipase at pH 9 in the absence of detergent, and shows washing performance in the form of a wild-type. The lipases may further provide additional benefits, such as it has potential benefits in baking. The amino acid sequence of this new lipase has a low identity compared with a known lipase as SEQ ID NO: 12 (44.4%). A search was made for the comparison of the DNA of this new lipase with the known sequences, and it was found that the highest homology with various *Fusarium* lipases (*F. heterosporum, F. oxysporum, F. sulphureum, F. venenatum, F. graminarum, F. culmorum, F. solani*) was 55-60% suggesting it is a new lipase.

The present invention relates to an isolated polypeptide having lipase activity selected from the group consisting of:
(a) a polypeptide comprising an amino acid sequence having at least 60% identity to the mature polypeptide of SEQ ID NO: 2;
(b) a polypeptide having an amino acid sequence which has at least 60% identity with amino acids 1 to 315 of SEQ ID NO: 2;
(c) a polypeptide encoded by a polynucleotide that hybridizes under at least low stringency conditions with (i) the mature polypeptide coding sequence of SEQ ID NO: 1, (ii) the cDNA sequence contained in or the genomic DNA sequence comprising the mature polypeptide coding sequence of SEQ ID NO: 1, or (iii) a full-length complementary strand of (i) or (ii);
(d) a polypeptide which is encoded by a polynucleotide which hybridizes under at least low stringency conditions with (i) nucleotides 41 to 1069 of SEQ ID NO: 1, (ii) the cDNA sequence contained in or the genomic DNA sequence comprising nucleotides 41 to 1069 of SEQ ID NO: 1, or (iii) a full-length complementary strand of (i) or (ii);
(e) a polypeptide which is encoded by a polynucleotide which hybridizes under at least low stringency conditions with nucleotides 41 to 1069 of SEQ ID NO: 1, or a complementary strand of nucleotides 41 to 1069 of SEQ ID NO: 1;
(f) a polypeptide encoded by a polynucleotide comprising a nucleotide sequence having at least 60% identity to the mature polypeptide coding sequence of SEQ ID NO: 1;
(g) a polypeptide derived from SEQ ID NO: 2 by substitution, deletion or addition of one or more amino acids;
(h) a polypeptide which has at least 60% identity with the polypeptide encoded by the polynucleotide contained in the plasmid which is contained in *E. coli* DSM 17467.

In a preferred aspect, the mature polypeptide is amino acids 1 to 315 of SEQ ID NO: 2. In another preferred aspect, the mature polypeptide coding sequence is nucleotides 41 to 1069 of SEQ ID NO: 1.

In another aspect the invention relates to a method for production of the polypeptide of the invention.

In a further aspect the invention relates to an isolated polynucleotide comprising a nucleotide sequence which encodes the polypeptide of the invention, to a recombinant host cell comprising said nucleic acid construct, and to a recombinant expression vector comprising said nucleic acid construct.

In a further aspect the invention relates to the use of the polypeptide of the invention in baking, and to a baking composition comprising the polypeptide of the invention.

DEFINITIONS

Lipase activity: The term "lipase activity" is defined herein as a lipolytic activity which hydrolyses the carboxylic ester bond in glyceryl tributyrate, olein, pNP-butyrate and pNP-palmitate (triacylglycerol lipase, EC 3.1.1.3).

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Mature polypeptide: The term "mature polypeptide" is defined herein as a polypeptide having lipase activity that is in its final form following translation and any post-translational modifications, such as N-terminal processing, C-terminal truncation, glycosylation, phosphorylation, etc. In a preferred aspect, the mature polypeptide is amino acids 1 to 315 of SEQ ID NO: 2.

Mature polypeptide coding sequence: The term "mature polypeptide coding sequence" is defined herein as a nucleotide sequence that encodes a mature polypeptide having lipase activity. In a preferred aspect, the mature polypeptide coding sequence is nucleotides 41 to 1069 of SEQ ID NO: 1.

Identity: The relatedness between two amino acid sequences or between two nucleotide sequences is described by the parameter "identity".

In one embodiment and for purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; amino acids 1 to 343 of SEQ ID NO: 2) and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|". The length of a sequence is the number of amino acid residues in the sequence (e.g. the length of SEQ ID NO: 2 is 343).

In the alignment example below, the overlap is the amino acid sequence "HTWGERNL" of Sequence 1; or the amino acid sequence "HGWGEDANL" of Sequence 2. In the example a gap is indicated by a "-".

Hypothetical Alignment Example

```
Sequence 1:        ACMSHTWGER-NL
                      | ||| ||
Sequence 2:        HGWGEDANLAMNPS
```

In another embodiment of the invention the degree of identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite (2000). Rice, P., Longden, I., and Bleasby, A. Trends in Genetics 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS, The European Molecular Biology Open Software Suite (2000). Rice, P., Longden, I., and Bleasby. A, Trends in Genetics 16, (6) p 276-277; http://emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in Bioinformatics Methods and Protocols, S. Misener and S. A. Krawetz, ed., pp. 185-219) with the mature lipase comprised in SEQ ID NO: 2 or the mature polypeptide encoding sequence comprised in SEQ ID NO: 1 as the case may be.

Polypeptide fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has lipase activity.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having lipase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively or recombinantly associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product.

Expression: The term "expression" includes any step involved in the production of the polypeptide, including, but not limited to, transcription, post-transcriptional modification, translation, post-translational modification, and secretion.

cDNA: The term "cDNA" is defined herein as a DNA molecule which lacks intron sequences that are usually present in the corresponding genomic DNA. The cDNA can be prepared by reverse transcription from a mature, spliced, mRNA molecule obtained from a eukaryotic cell. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequences: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction and the like with a nucleic acid construct comprising a polynucleotide of the present invention.

Artificial variant: When used herein, the term "artificial variant" means a polypeptide having lipase activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptide of the Invention

The ratio of the substrate specificity (pNPC4/C16) of the lipase of the present invention to a known lipase as SEQ ID NO: 12 is 0.5.

The lipase of the present invention shows activity in the temperature range from 20° C. to 50° C. with an optimum at 30° C., and an optimum at pH 9. The pH- and thermo-stability test showed that it was stable at pH 10 up to 30 minutes, and the residual activity was 44.7% and 36.1% respectively after incubation at 40° C. for 30 minutes or 50° C. for 20 minutes.

The malodour usually forms under drying conditions subsequent to washing especially due to cleavage of short-chained glycerides in milk fat. Thus, one way to solve the malodour problem is looking for a first wash lipase which is very active on the long-chained glycerides at high pH (7.0-11.0) but has low activity on short-chained glycerides, for example, triburyrin, at pH 7.0-9.0. The lipase of the present invention showed high lipase activity towards olive oil at pH 10.0 and better substrate specificity (a tower ratio on pNPC4, pH 7.0 to pNPC16) compared with the known lipase of SEQ ID NO: 12.

Polypeptides Having Lipase Activity

The lipase of the present invention is a lipase which may be purified from the fungal strain *Nectria* sp.

In one aspect the present invention relates to isolated polypeptides comprising an amino acid sequence having a degree of identity to the mature polypeptide of SEQ ID NO: 2 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, or 99%, which have lipase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

In an embodiment the polypeptide of the invention comprises or consists of the mature polypeptide of SEQ ID NO: 2; or a fragment thereof having lipase activity.

In a further aspect, the present invention relates to isolated polypeptides having an amino acid sequence which has a degree of identity to amino acids 1-315 of SEQ ID NO: 2 or with the polypeptide encoded by the polynucleotide contained in the plasmid which is contained in *E. coli* DSM 17467 (i.e., the mature polypeptide) of at least 60%, preferably at least 65%, more preferably at least 70%, more preferably at least 75%, more preferably at least 80%, more preferably at least 85%, even more preferably at least 90%, such as 91%, or 92%, or 93%, or 94%, most preferably at least 95%, such as 96%, or 97%, or 98%, or 99% (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 1-315 of SEQ ID NO: 2.

In an embodiment the polypeptide of the invention comprises or consists of the amino acids 1 to 315 of SEQ ID NO: 2; or a fragment thereof having lipase activity.

In an embodiment the polypeptide of the invention is encoded by a polynucleotide that hybridizes under at least medium stringency, at least medium-high stringency or at least high stringency conditions with (i) the mature polypeptide coding sequence of SEQ ID NO: 1, (ii) the cDNA sequence contained in or the genomic DNA sequence comprising the mature polypeptide coding sequence of SEQ ID NO: 1, or (iii) a full-length complementary strand of (i) or (ii).

In an embodiment the polypeptide of the invention is encoded by a polynucleotide comprising a nucleotide sequence having at least 65%, 70%, 75%, 80%, 85%, 90% or 95% identity to the mature polypeptide coding sequence of SEQ ID NO: 1

In an embodiment the polypeptide of the invention is encoded by a polynucleotide comprising or consisting of the nucleotide sequence of SEQ ID NO: 1; or a subsequence thereof encoding a fragment having lipase activity.

In an embodiment the polypeptide of the invention is encoded by a polynucleotide comprising or consisting of the mature polypeptide coding sequence of SEQ ID NO: 1.

In an embodiment the polypeptide of the invention is encoded by a polynucleotide comprising or consisting of the nucleotide sequence of SEQ ID NO: 1.

In a further aspect, the present invention relates to isolated polypeptides having lipase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 41 to 1069 of SEQ ID NO: 1, (ii) the cDNA sequence contained in nucleotides 41 to 1069 of SEQ ID NO: 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has lipase activity.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[\text{Na}^+]) + 0.41(\%G + C) - 0.72(\% \text{ formamide})$$

A 1% mismatch of two DNAs lowers the $T_m$ by 1.4° C. To determine the degree of identity required for two DNAs to hybridize under medium stringency conditions at 42° C., the following formula is used:

$$\% \text{ Homology} = 100 - [(\text{Effective } T_m - \text{Hybridization Temperature})/1.4]$$

In a further aspect, the present invention relates to isolated polypeptides having lipase activity encoded by a polynucleotide comprising nucleotides 41 to 1069 of SEQ ID NO: 1, as a unique motif.

In a further aspect, the present invention relates to artificial variants comprising a conservative substitution, deletion, and/or insertion of one or more of the amino acids 1-315 of SEQ ID NO: 2 or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and asparic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, in, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

The total number of amino acid substitutions, deletions and/or insertions of amino acids of the mature part of SEQ ID NO: 2 is 10, preferably 9, more preferably 8, more preferably 7, more preferably at most 6, more preferably at most 5, more preferably 4, even more preferably 3, most preferably 2, and even most preferably 1.

Polynucleotides

The present invention also relates to isolated polynucleotides having a nucleotide sequence which encode a polypeptide of the present invention. In a preferred aspect, the nucleotide sequence is set forth in SEQ ID NO: 1. In another more preferred aspect, the nucleotide sequence is the sequence contained in *E. Coli* DSM 17467. In another preferred aspect, the nucleotide sequence is the mature polypeptide coding region of SEQ ID NO: 1. The present invention also encompasses nucleotide sequences which encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 which encodes fragments of SEQ ID NO: 2 that have lipase activity.

The present invention also relates to mutant polynucleotides comprising at least one difference in the mature polypeptide coding sequence of SEQ ID NO: 1, in which the mutant nucleotide sequence encodes a polypeptide which consists of amino acids of SEQ ID NO: 2.

In an embodiment the isolated polynucleotide of the invention comprises at least one mutation in the mature polypeptide coding sequence of SEQ ID NO: 1, in which the mutant nucleotide sequence encodes the mature polypeptide of SEQ ID NO: 2

In an embodiment the isolated polynucleotide of the invention is obtained by
(a) hybridizing a population of DNA under at least low stringency, at least medium stringency, at least medium-high stringency or at least high stringency conditions with (i) the mature polypeptide coding sequence of SEQ ID NO: 1, (ii) the cDNA sequence contained in or the genomic DNA sequence comprising the mature polypeptide coding sequence of SEQ ID NO: 1, or (iii) a full-length complementary strand of (i) or (ii); and
(b) isolating the hybridizing polynucleotide, which encodes a polypeptide having lipase activity.

The present invention also relates to polynucleotides having nucleotide sequences which have a degree of identity to the mature polypeptide coding sequence of SEQ ID NO: 1 (i.e., nucleotides 41 to 1069) of at least 40, preferably at least 50, preferably at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

In a preferred aspect, the host cell is a fungal cell, in particular a fungal cell, such as a yeast cell or a filamentous cell, e.g. a strain of *Aspergillus, Fusarium, Trichoderma* or *Saccharomyces*, particularly *A. niger, A. oryzae, F. grimnearum* or *S. cerevisiae*.

Methods of Production

The present invention also relates to methods for producing a polypeptide of the present invention, comprising cultivating a cell, harboring a polynucleotide encoding the polypeptide of the invention, under conditions conducive for production of the polypeptide; and recovering the polypeptide.

In an embodiment the cell is the recombinant host cell of claim. In another embodiment the cell is a wild type cell.

Compositions

The present invention also relates to compositions comprising a polypeptide of the present invention. Preferably, the compositions are enriched in such a polypeptide. The term "enriched" indicates that the lipase activity of the composition has been increased, e.g., with an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergilus foetidus, Aspergillus japonicus, Aspergilus nidulans, Aspergilus niger*, or *Aspergillus oryzaee; Fusarium*, preferably *Fusarium bactridiodes, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusaritum roseum, Fusarium sambucinun, Fusarium sarcochrouim, Fusarium sulphureum, Fusarium toruloseum, Fusarium trichlotheciodes*, or *Fusarium venenatum; Humicola*, preferably *Humicola insolens* or *Humicola lanuginosa*; or *Trichoderma*, preferably *Trichoderma harzianum, Trichoderma koningii, Trichoderma longibrachiatum, Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Detergent Applications

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

Enzymes

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 68, 76, 87, 97, 101, 104, 106, 120, 123, 167, 170, 194, 206, 218, 222, 224, 235, 245, 252 and 274, and amongst other variants with the following mutations: (K27R, V104Y, N123S, T124A), (N76D, S103A, V104I), or (S101G, S103A, V104I, G159D, A232V, Q236H, Q245R, N248D, N252K).

Preferred commercially available protease enzymes include Alcalase™, Savinase™, Primase™, Duralase™, Esperase™, Coronase™, Polarzyme™ and Kannase™ (Novozymes A/S), Maxatase™, Maxacal™, Maxapem™, Properase™, Purafect™, Purafect Prime™, Purafect OxP™, FN2, FN3 and FN4 (Genencor International Inc.).

Lipases

Lipases include those of bacterial or fungal origin. Chemically modified or protein engineered mutants are included. Examples of useful lipases include lipases from *Humicola* (synonym Thermomyces), e.g. from *H. lanuginosa* (synonymous *T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (ER 331 376), *P. stutzere* (GB 1,372,034), *P. fluorescens, Pseudomonas* sp. strain SD 705 (WO 95/06720 and WO 96/27002), *P. wisconsinensis* (WO 96/12012), a *Bacilus* lipase, e.g. from *B. subtilis* (Dartois et al. (1993), Biochemica et Biophysica Acta, 1131, 253-360), *B. stearothermophilus* (JR 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615 WO 97/04079 and WO 97/07202.

Other commercially available lipase enzymes include Lipolase™, Lipolase Ultra™ and Lipex™ (Novozymes A/S).

Preferred lipases are lipases of the present invention.

Amylases

Suitable amylases (alpha and/or beta) include those of bacterial or fungal origin. Chemically modified or protein engineered mutants are included. Amylases include, for example, alpha-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Stainzyme™, Stainzyme Ultra™, Fungamyl™ and BAN™ (Novozymes A/S), Rapidase™ and Purastar™ (from Genencor International Inc.).

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Renozyme™, Celluzyme™, and Carezyme™ (Novozymes A/S), Clazinase™, and Puradax HA™ (Genencor International Inc.), and KAC-500(B)™ (Kao Corporation).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

Detergents

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units: fatty alcohols; fatty acids, and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0% to 60% by weight.

When included therein the detergent will usually contain from about 0% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.001-100 mg of enzyme protein per liter of wash liquor, such as 0.01-50 mg or 0.03-30 mg, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202, WO 04/041979, and WO 04/074419, which is hereby incorporated as reference.

Baking

In a specific embodiment the enzyme of the present invention is used for baking.

Dough

The dough of the invention generally comprises wheat meal or wheat flour and/or other types of meal, flour or starch such as corn flour, corn starch, rye meal, rye flour, oat flour, oat meal, soy flour, sorghum meal, sorghum flour, potato meal, potato flour or potato starch. The dough of the invention may be fresh, frozen or par-baked.

The dough of the invention is normally leavened dough or dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (bakers yeast), e.g. a commercially available strain of *S. cerevisiae*.

The dough may also comprise other conventional dough ingredients, e.g.: proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat (triglyceride) such as granulated fat or shortening, but the invention is particularly applicable to a dough where less than 1% by weight of fat (triglyceride) is added, and particularly to a dough which is made without addition of fat. The dough may further comprise an emulsifier such as mono- or diglycerrides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysotecithin.

Additional Enzyme

Optionally, an additional enzyme may be used together with the lipase. The additional enzyme may be an amylase, such as an a maltogenic amylase, amy-loglucosidase, a beta-amylase, a cyclodextrin glucanotransferase, or the additional enzyme may be a peptidase, in particular an exopeptidase, a transglutaminase, a lipotytic enzyme, a cellulase, a hemicellulase, in particular a pentosanase such as xylanase, a protease, a protein disulfide isomerase, e.g., a protein disulfide isomerase as disclosed in WO 95/00636, a glycosyltransferase, a branching enzyme (1,4-alpha-glucan branching enzyme), a 4-alpha-glucanotransferase (dextrin glycosyltransferase) or an oxidoreductase, e.g., a peroxidase, a lassase, a glucose oxidase, a pyranose, oxidases, a lipoxygenase, an L-amino acid oxidase or a carbohydrate oxidase.

The additional enzyme may be of any origin, including mammalian and plant, and preferably of microbial (bacterial, yeast or fungal) origin and may be obtained by techniques conventionally used in the art.

The maltogenic amylase may be derived from *Bacillus stearothermiphilus* as described in EP 494233 or a variant thereof as described in WO 99/43794.

The lipolytic enzyme may have lipase activity (EC 3.1.1.3), phospholipase A1 activity, phospholipase A2 activity and/or galactolipase activity.

Baked Product

The process of the invention may be used for any kind of baked product pre-pared from dough, either of a soft or a crisp character, either of a white, light or dark type. Examples are bread (in particular white, whole-meal or rye bread), typically in the form of loaves or rolls, French Baguette-type bread, pita bread, tortillas, cakes, pancakes, biscuits, cookies, pie crusts, crisp bread, steamed bread, pizza and the like.

Baking Composition

The present invention further relates to a baking composition comprising flour together with the polypeptide of the invention. The baking composition may contain other dough-improving and/or bread-improving additives, e.g. any of the additives, including enzymes, mentioned above.

Enzyme Preparation

The invention provides an enzyme preparation comprising a lipase, for use as a baking additive in the process of the invention. The enzyme preparation is preferably in the form of a granulate or agglomerated powder. It preferably has a narrow particle size distribution with more than 95% (by weight) of the particles in the range from 25 to 500 micro-m.

Granulates and agglomerated powders may be prepared by conventional methods, e.g. by spraying the amylase onto a carrier in a fluid-bed granulator. The carrier may consist of particulate cores having a suitable particle size. The carrier may be soluble or insoluble, e.g. a salt (such as sodium chloride or sodium sulfate), a sugar (such as sucrose or lactose), a sugar alcohol (such as sorbitol), starch, rice, corn grits, or soy.

Uses

The present invention also relates to the uses of the lipase in the manufacture of detergent and in baking.

The enzyme of the invention can be used in known applications of lipolytic enzymes by analogy with the prior art, e.g.:

An enzyme with lipase activity can be used in the pulp and paper industry, to remove pitch or to remove ink from used paper. WO 9213130, WO 9207138, JP 2160984 A, EP 374700.

An enzyme with phospholipase activity can be used in a process for reducing the content of phospholipid in edible oil. U.S. Pat. No. 5,264,367 (Metallgesellschaft, Röhm); K. Dahike & H. Buchold, INFORM, 6 (12), 1284-91 (1995); H. Buchold, Fat Sci. Technol., 95 (8), 300-304 (1993); JP-A 2-153997 (Showa Sangyo); or EP 654,527 (Metallgeseitschaft, Röhm).

An enzyme with lysophospholipase activity can be used to improve the filterability of an aqueous solution or slurry of carbohydrate origin, e.g. starch hydrolysate, especially a wheat starch hydrolysate. EP 219,269.

An enzyme with phospholipase activity, can be used for the preparation of lysophospholipid, e.g. lyso-lecithin (EP 870840, JP-A 10-42884, JP-A 4-135456 or JP-A 2-49593) of for the production of mayonnaise (EP 628256, EP 398666 or ER 319064).

An enzyme with phospholipase activity, may also be used in the processing of dairy and other food products, e.g. as described in EP 567,662 (Nestle), EP 426,211 (Unilever), EP 166,284 (Nestlé) JP-A 57-189638 (Yakult) or U.S. Pat. No. 4,119,564 (Unile-ver).

An enzyme with phospholipase activity can be used in the leather industry, GB 2233665, EP 505920.

An enzyme with lipase activity may be used for removing fatty matter containing hydrophobic esters (e.g. triglycerides) during the finishing of textiles, WO 93/13256.

The present invention is further described by the following examples which should not be construed as limiting the scope of the invention.

EXAMPLES

Chemicals used as buffers and substrates were commercial products of at least reagent grade.

Media and Solutions

Fungal Strain:

*Nectria* sp is a mesophilic strain isolated from plant samples and with good growth in media at neutral pH.

Media for Fungal Growth

YS-25 with the following composition: 1 L medium contained 10 g peptone, 10 g yeast extract, 5 g glucose, 5 g K2HPO4, 1 g MgSO4×7H2O and 20 ml olive oil. After the pH was adjusted to 6.5, the medium was autoclaved at 121 for 20 minutes, Substrates Olive oil, Tributyrin, pNP-palmitate, pNP-butyrate Chemicals Agar, Triton X-100, gum Arabic, sodium phosphate, Citric acid, PVA, Brilliant green, Ariel colour compact (CHN-2003-00294), Tris-HCI, PMSF and EDTA.

Example 1

The Production of the Lipase of the Present Invention Cloned from *Nectria* Strain Material and Method Materials:

Oligonucleotide primers for polymerase chain reaction (PCR) were custom-made by Shanghai Sangon Biological Engineering & Technology and Service Co. Ltd. The RNeasy Mini Kit was purchased from Oiagen company. The Taq DNA polymerase from Fermentas company. The pGEM-T Vector System I and Wizard Plus Minipreps DNA Purification System were purchased from Promega company. The 3' Rapid Amplification of cDNA End System and HIFI Taq DNA polymerase were purchased from Invitrogen company. DNA Walking SpeedUp Kit was purchased from Seegene. The DNA Marker: 100 bp DNA ladder was purchased from New England Biolab.

Fungal Strain:

*Nectria* sp. strain was isolated from China

Fermentation and Mycelium Harvesting:

4-6 agar plugs with fully grown fungal cultures on the PDA plates were used to inoculate one shake flask with YS-25 medium with olive oil and incubated under room temperature, 160 rpm for 144 hours. Mycelium was harvested by filtering against miracloth and squeezing dry. It was quickly frozen in liquid N2 and stored at −80° C.

Gene Cloning:

1. Primer design 1.1. Primers designed based on n-terminal sequence.

Two degenerate primers was designed based on N-terminal sequence of the lipase of the present invention; AVTVTSQN-LANFKFY VQHAT

```
Lipase n1:
                                    (SEQ ID NO.: 8)
5' ca(ag) aa(tc) (ct)tn gcn aa(tc) tt 3'

Lipase n2:
                                    (SEQ ID NO.: 9)
5' aa(tc) tt(tc) ta(tc) gtn ca(ag) ca(tc) gc 3'
```

1.2. Reverse (antisense) primers designed based on the conserved region of fusarium lipases

```
                                    (SEQ ID NO.: 10)
lipFDR1: 5' agg ttg gc(ag) gc(ag) ccc tca ca 3'

(SEQ ID NO.: 11)
lipFDR2: 5' g(at)(at) gtg tgc c(gt)g tat cca aa 3'
```

2. Total RNA preparation and cDNA synthesis

The total RNA was isolated by using The RNeasy Mini Kit. The cDNA was synthesized by following the instruction of 3' Rapid Amplification of cDNA End System (3' RACE).

3. PCR amplification:

3.1 partial gene cloning

The first PCR was performed by using lipase-η1 and AUAP (5'-GGCCACGCGTCG ACTAGTAC-3', supplied by 3' RACE kit) as primer pair and cDNA as template. The detailed the procedure is:

| | |
|---|---|
| 10× PCR buffer | 5 ul |
| 25 mM MgCl2 | 3 ul |
| 10 mM dNTP | 1 ul |
| 100 uM lipase-1 n1 | 1 ul |
| cDNA | 2 ul |
| Taq | 1 ul |
| H2O | 36 ul |

First step, without the reverse primer AUAP, after 94° C. for 3 min. 4 cycles of 94° C. for 40 secs, 42° C. for 1 mins and 72° C. for 1 mins.

Second step: with the addition of 1 ul of denatured AUAP (95° C. for 5 mins and leaving on ice), 35 cycles of 94° C. for 40 secs, 48° C. for 40 secs and 72° C. for 1 min, final extension at 72° C. for 10 mins.

The nested PCR was performed by using primer pair lipase-n1 and lipFDR1 and the first PCR solution as template.

| | |
|---|---|
| 10× PCR buffer | 5 ul |
| 25 mM MgCl2 | 3 ul |
| 10 mM dNTP | 1 ul |
| 100 uM lipase-n1 | 1 ul |
| 100 uM lipFDR1 | 1 ul |
| 100× diluted 1st PCR solution | 5 ul |
| Taq | 1 ul |
| $H_2O$ | 36 ul |

The PCR program as: 94° C. for 3 min; 35 cycles of 94° C. for 40 secs, 50° C. for 40 secs, 72° C. for 1 min; final extension at 72° C. for 10 min.

A specific amplification at ~700 base pairs was recovered from gel and directly sequenced. It was confirmed to be a lipase. Based on this partial sequence new primers were designed for 5' end cloning (coding region for signal and propeptide):

```
                                              (SEQ ID NO.: 3)
Lipase-as1: 5' tcc aga cga agt cga ggt ttg tga 3'

(SEQ ID NO.: 4)
Lipase-as2: 5' tac tgc cac gga tag aga cga caa 3'

(SEQ ID NO.: 5)
Lipase-as3: 5' cat gcc cgt atc ctc gcc tcc gaa 3'
```

3.2 5' end cloning

For 5' end cloning, the DW-ACP (DNA Walking-Annealing Control Primer) PCR was performed with the DNA Waking SpeedUp kit. The first PCR was performed with primer pair lipase-as1 with 4 DW-ACP primers: DW-ACP1,2,3,4 (supplied by DNA Waking SpeedUp kt) separately.

```
        DW-ACP1:        5'-ACP-AGGTC-3'

DW-ACP2:        5'-ACP-TGGTC-3'

DW-ACP3:        5'-ACP-GGGTC-3'

DW-ACP4:        5-ACP-CGGTC-3'
```

The PCR program is: 1 cycle of 94° C. for 5 mins, 42° C. for 1 min, 72° C. for 3 mins; 35 cycles of 94° C. for 40 secs, 55° C. for 40 secs and 72° C. for 45 secs; final extension at 72° C. for 7 mins.

Nested PCR was performed with primer pair lipase-as2 and the Universal primer (5'-TCA CAG AAG TAT GCC AAG CGA-3', supplied by DNA Waking SpeedUp kt), and 100× diluted 1st PCR solution as template. The PCR program is 94° C. for 3 mins, 10 cycles of 94° C. for 40 secs, 65° C. for 40 secs (decrease 1° C. per cycle) and 72° C. for 45 secs, 29 cycles of 94° C. for 40 secs, 55° C. for 40 secs and 72° C. for 45 secs; final extension at 72° C. for 10 mins.

A specific amplification of about 1 kb was obtained from the nested PCR by lipase-as2 and universal primer as primer pairs and 1st PCR solution (by DW-ACP4 and lipase-as1) as template. It was identified as the 5' end of lipase. Then the 5' end primers were designed for full length cloning:

```
                                              (SEQ ID NO.: 6)
lipase-s00:   5' aac agg acc cct aga ctt gtg t 3'

(SEQ ID NO.: 7)
lipase-s01:   5' taa ctc tcc tga ttc tca ca 3'
```

3.3 Full length cloning from cDNA

Finally, the full length gene was cloned by PCR with lipase-s00 and AUAP by using HIFI Taq DNA polymerase. The PCR program was: 94° C., 3 mins; 10 cycles of 94° C. for 40 secs, 60° C. 40 secs with 1° C. decrease per cycle, 72° C. for 1 min; 20 cycles of 94° C. for 40 secs, 50° C. for 40 secs, 72° C. for 1 min; final extension at 72° C. for 10 mins. A specific fragment at 1.2 kb was amplified. It was identified as a lipase.

The obtained PCR fragment was cloned into pGEM-T vector and transformed into *E. coli* DH10B. The positive clones were selected for plasmid preparation for sequencing.

1. Full length PCR amplification of lipase of present application was identified as expected.

2. Full length sequence of the lipase of the present invention.

The full length gene fragment was sequenced and registered into Bioweb. The coding region of this cloned the lipase of the present invention includes 1032 base pairs including stop codon as shown in SEQ ID NO: 1.

Identity search showed 44% identity to lipase from *Thermomyces lanuginosus* (*Humicola lanuginosa*) or 58% to *Acremonium butyri* lipase.

Example 2

The Purification of the Lipase of the Present Invention

1. The (NH4)2SO4 precipitated proteins were dialysed against 25 mM Tris-HCl buffer (pH 7.0) to a conductivity lower than 1 ms/cm.

2. The dialysed proteins were loaded on a Fast Flow Q column, with a column volume (CV) of 55 ml, and eluted with 25 mM Bis-Tris buffer (pH 7.0) containing 1M NaCl. The fractions with lipase activity on olive oil plate at pH 9 were pooled. Two lipase activities were separated in salt gradient 0.056-0.069M and 0.095-0.113M.

3. Lipase fractions, which were eluted from the linear gradient of 0.095-0.113M NaCl on QFF column, were further purified by a Mono Q HR16/10 column. The lipase fractions were eluted with 25 mM Tris-HCl buffer, pH 7.0 with a linear gradient 0.175-0.187M NaCl.

4. Lipase fractions, obtained from Mono Q column, were further purified by a HiLoad 26/60 Superdex 75 (prep grade) column with 25 mM Tris-HCl buffer, pH 7.0 containing 0.15M NaCl.

5. Pooled lipase activity from Step 4 was loaded on a MonoQ HR16/10 column, and eluted with 25 mM Tris-HCl buffer, pH 8.0 with a NaCl gradient of 0.227-0.238M. The purification of the lipase of the present invention was examined by SDS-PAGE.

13.4 L culture broth was obtained from 278 shake flasks. The total sample volume after dialysis was 600 ml. The SDS-PAGE indicated that the pooled the lipase of the present invention fractions contained one protein band at molecular weight of 29 kD. Totally 9.8 mg pure protein was obtained.

Example 3

Characterization of the Lipase of the Present Invention

1. Determination of Optimum Temperature

The optimum temperature of the lipase of the present invention has been determined as 30 by pNP-palmitate (pNPC16) assay as described in 'Substrate specificity'.

2. Determination of Optimum pH

The optimum pH of the lipase of the present invention was pH 9 as determined by pNP-palmitate assay as described in 'Substrate specificity'. The lipase of the present invention showed pH profile similar to the lipase of SEQ ID NO: 12.

3. Substrate Specificity

Determination of Substrate Specificity:

The substrate specificity of lipase on triglyceride was expressed by a ratio of enzyme activity on pNP-butyrate (pNPC4) and pNP-palitimate (pNPC16) by applying the following steps:

1. Substrate stock: The substrate, pNPC4 or pNPC16, was dissolved in 1-propanol to a final concentration of 16.5 mM.
2. The reaction buffer for pNP-C4 was 50 mM Tris-HCl (pH7.0) containing 0.4% (w/v) Triton X100, 0.1% (w/v) arabic gum, 2 mM EDTA and 2 mM PMSF. The reaction buffer for pNP-C16 was 0.1M glycine (pH9.0), containing 0.4% (w/v) Triton X100, 0.1% (w/v) arabic gum, 2 mM EDTA and 2 mM PMSF.
3. The substrate working solution was made up by mixing one volume of stock solution with nine volume of reaction buffer just prior to use.
4. The reaction was started by mixing 20 micro-L sample or blank or control and 150 micro-L of substrate working solution.
5. The reaction was monitored for 5 min by following the absorbance change at 405 nm.
6. The ratio was calculated as mOD/min (pNPC4) divided by mOD/min (pNPC16).

The lipase of the present invention showed low activity on pNP-butyrate (pNPC4) at pH 7, The results are listed in Table 1:

TABLE 1

|  | The lipase of the present invention | Lipase with SEQ ID NO.: 12 |
|---|---|---|
| mOD/min(pNP-butyrate) | 47.46 | 93.86 |
| mOD/min(pNP-paltimate) | 348.93 | 336.86 |
| Ratio(pNPC4/pNPC16) | 0.136 | 0.278 |

4. Determination of pH Stability 10 ul of the lipase of the present invention was mixed with 190 ul of buffer. Then the mixed solution was incubated at 30° C. for 5, 10, 20 and 30 minutes respectively. After incubation the lipase activity was assayed using the pNP-palmitate assay (pH9, 30° C.).

When incubated with a buffer, the lipase of the present invention showed that it retained good residual activity in the range of pH 6-10 for at least 30 minutes at 30° C.

| Residual Activity | pH 6 | pH 7 | pH 8 | pH 9 | pH 10 |
|---|---|---|---|---|---|
| 5 min | 89% | 88% | 87% | 87% | 90% |
| 10 min | 77% | 73% | 73% | 79% | 82% |
| 20 min | 77% | 72% | 75% | 73% | 82% |
| 30 min | 85% | 81% | 82% | 82% | 84% |

The following buffers were used:
50 mM Bis-Tris, pH 6.0
50 mM Tris-HCl, pH 7.0
50 mM Tris-HCl, pH 8.0
0.1M Glycine, pH 9.0
0.1M Glycine, pH 10.0

5. Determination of Thermostability

The residual activity of the lipase of the present invention at pH 10 at different temperatures is listed below in table 2:

TABLE 2

|  | Control | 30° C. | 40° C. | 50° C. | 60° C. |
|---|---|---|---|---|---|
| 5 min | 390.53 | 377.13 | 342.27 | 288.33 | 5.67 |
|  |  | 96.6% | 86.7% | 73.8% | 13.2% |
| 10 min | 390.53 | 373.67 | 320.80 | 230.80 | 4.07 |
|  |  | 95.7% | 82.1% | 59.1% | 1.0% |
| 15 min | 387.77 | 328.63 | 262.57 | 152.57 | −2.57 |
|  |  | 84.7% | 67.7% | 39.3% | n.a. |
| 20 min | 387.77 | 325.30 | 256.50 | 139.97 | −1.37 |
|  |  | 83.9% | 66.2% | 36.1% | n.a. |
| 30 min | 434.27 | 306.07 | 194.27 | 81.93 | −1.00 |
|  |  | 70.5% | 44.7% | 18.9% | n.a. |

0.1M Glycine buffer was used.

6. N-terminal Sequence

The 20 amino acid sequence at N-terminal was AVTVTSQNLANFKFYVQHAT.

Example 4

Lipase Activity Determined By Substrate-Agar Assay

Oil emulsion: 50 ml olive oil was added into 150 ml 2% PVA (polyvinyl alcohol), then emulsified with Ultra-Turrax.

100 ml of 2% agar was mixed with 91 ml phosphate citrate buffer (pH7.0 or 9.0), 8 ml oil emulsion and 1 ml of 1% Brilliant Green. The above solutions have been either cooled down or warmed up to 60°. The mixed solution was poured into petri dishes. After the agar mixture was set, the sample holes (3 mm in diameter) were punched in a distance of 1 cm next to each other. 20 micro-L of supernatant was applied in each sample hole, and the plate was incubated at room temperature overnight. The activity was detected as a green zone around the sample hole in the plate.

Example 5

AMSA—Automated Mechanical Stress Assay—for Calculation of RP

The enzyme of the present application may be tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24. The containers, which contain the detergent test solution, consist of cylindrical holes (6 mm diameter, 10 mm depth) in a metal plate. The stained fabric (test material) lies on the top of the metal plates and is used as a lid and seal on the containers. Another metal plate lies on the top of the stained fabric to avoid any spillage from each container. The two metal plates together with the stained fabric are vibrated up and down at a frequency of 30 Hz with an amplitude of 2 mm.

The assay is conducted under the experimental conditions specified below:

TABLE 3

| Test solution | 0.5 g/l LAS |
|---|---|
|  | 0.52 g/l Na2CO3 |
|  | 1.07 g/l Zeolite A |
|  | 0.52 g/l Na3Citrate |

TABLE 3-continued

| | |
|---|---|
| Test solution volume | 160 micro l |
| pH | As is (~9.9) |
| Wash time | 20 minutes |
| Temperature | 30° C. |
| Water hardness | 15° dH<br>Ratio of $Ca^{2+}/Mg^{2+}/NaHCO_3$:4:1:7:5 |
| Enzyme concentration in test solution | 0.125, 0.25, 0.50, 1.0 mg ep/l |
| Drying | Wash performance: After washing the textile pieces is immediately flushed in tap water and air-dried at 85 C. in 5 min<br>Odour: After washing the textile pieces is immediately flushed in tap water and dried at room temperature (20° C.) for 2 hours |
| Test material | Cream turmeric swatch as described below (EMPA221 used as cotton textile) |

Cream-turmeric swatches are prepared by mixing 5 g of turmeric (Santa Maria, Denmark) with 100 g cream (38% fat, Arla, Denmark) at 50° C., the mixture is left at this temperature for about 20 minutes and filtered (50° C.) to remove any un-dissolved particles. The mixture is cooled to 20° C. and woven cotton swatches, EMPA221, are immersed in the cream-turmeric mixture and afterwards allowed to dry at room temperature over night and frozen until use.

The performance of the lipase is measured as the brightness of the colour of the textile samples washed with the lipase. Brightness can also be expressed as the intensity of the light reflected from the textile sample when illuminated with white light. When the textile is stained the intensity of the reflected light is lower, than that of a clean textile. Therefore the intensity of the reflected light can be used to measure wash performance of an enzyme variant.

Color measurements are made with a professional flatbed scanner (PFU DL2400pro), which is used to capture an image of the washed textile samples. The scans are made with a resolution of 200 dpi and with an output color depth of 24 bits. In order to get accurate results, the scanner is frequently calibrated with a Kodak reflective IT8 target.

To extract a value for the light intensity from the scanned images, a program is used that retrieves the 24 bit pixel values from the image and converts them into values for red, green and blue (RGB). The intensity value (int) is calculated by adding the RGB values together as vectors and then taking the length of the resulting vector:

$$Int = \sqrt{r^2 + g^2 + g^2}.$$

The wash performance (P) of the variants is calculated in accordance with the below formula:

$$P = Int(v) - Int(r)$$

where

Int(v) is the light intensity value of textile surface washed with enzyme, and

Int(r) is the light intensity value of textile surface washed without enzyme.

A relative performance score is given as the result of the AMSA wash in accordance with the definition:

Relative Performance scores (RP) are summing up the performances (P) of the tested enzyme variants against the reference enzyme (SEQ ID NO: 12):

$$RP = P(\text{test enzyme})/P(\text{reference enzyme}).$$

RPavg indicates the average relative performance compared to the reference enzyme at all three enzyme concentrations (0.125, 0.25, 0.5, 1.0 mg ep/l)

$$RPavg = avg(RP(0.125), RP(0.25) RP(0.5), RP(1.0))$$

A lipase is considered to exhibit improved wash performances if it performs better than the reference.

Example 6

GC—Gas Chromatograph—for Calculation of Risk Factor

The butyric acid release from the lipase washed swatches are measured by Solid Phase Micro Extraction Gas Chromatography (SPME-GC) using the following method: Four textile pieces (5 mm in diameter), washed in the specified solution in Table 1 containing 1 mg/L lipase, are transferred to a Gas Chromatograph (GC) vial. The samples are analysed on a Varian 3800 GC equipped with a Stabilwax-DA W/Integra-Guard column (30 m, 0.32 mm ID and 0.25 micro-m df) and a Carboxen PDMS SPME fibre (75 micro-m). Each sample is preincubated for 10 minutes at 40° C. followed by 20 minutes sampling with the SPME fibre in the head-space over the textile pieces. The sample is subsequently injected onto the column (injector temperature=250° C.), Column flow=2 ml Helium/min. Column oven temperature gradient: 0 min=40° C., 2 min=40° C., 22 min=240° C. 32 min=240° C. The butyric acid is detected by FID detection and the amount of butyric acid is calculated based on a butyric acid standard curve.

The Risk Performance Odour, R, of a lipase variant is the ratio between the amount of released butyric acid from the lipase of the invention washed swatch and the amount of released butyric acid from a swatch washed with the mature part of the reference lipase, after both values have been corrected for the amount of released butyric acid from a non-lipase washed swatch. The risk (R) of the variants is calculated in accordance with the below formula:

Odour=measured in ug buturic acid developed at 1 mg enzyme protein/I corrected for blank $$\alpha_{text\ enzyme} = Odour_{test\ enzyme} - Blank$$

$$\alpha_{reference\ enzyme} = Odour_{reference\ enzyme} - Blank$$

$$R = \alpha_{test\ enzyme} / \alpha_{reference\ enzyme}$$

A variant is considered to exhibit reduced odor compared to the reference (SEQ ID NO: 12): if the R factor is lower than 1.

Example 7

AMSA—Automated Mechanical Stress Assay—Results for Wash Performance and Odour A lipase enzyme of the present application was tested using the Automatic Mechanical Stress Assay (AMSA) in four different test solutions A), B), C), and D) in different concentrations of the enzyme. The assays for solutions A), B), C), and D) were conducted under the following experimental conditions:

| | |
|---|---|
| Test solutions A, B and C | A) 25 mM Glycine + 2 mM $CaCl_2$ (pH 8) |

| | | |
|---|---|---|
| | -continued | |
| | B) 25 mM Glycine + 2 mM CaCl$_2$ (pH 9) | |
| | C) 25 mM Glycine + 2 mM CaCl$_2$ (pH 10) | |
| Test solution volume | 160 micro l | |
| Wash time | 20 minutes | |
| Temperature | 25° C. | |
| Test enzyme (SEQ ID NO: 2) | 0.25, 0.5, 1.0, 2.0 mg enzyme protein per liter (ep/l) | |
| Reference enzyme (SEQ ID NO: 12) | 1.0 mg ep/l and 2.0 mg ep/l | |
| Drying | For calculating wash performance: After washing the textile pieces they were immediately flushed in tap water and air-dried at 85° C. for 5 minutes. For calculating Odor: After washing the textile pieces they were immediately flushed in tap water and dried at room temperature (20° C.) for 2 hours | |
| Test material | Cream turmeric swatch as described below (EMPA221 used as cotton textile) | |
| Test solution D | D) Commercial US liquid type detergent 0.79 g/L in water | |
| Test solution volume | 160 micro l | |
| pH | Not measured; given by the test soluton | |
| Wash time | 20 minutes | |
| Temperature | 30° C. | |
| Water hardness | 6° dH Ratio of Ca$^{2+}$/Mg$^{2+}$/NaHCO$_3$:2:1:4:5 | |
| Test enzyme (SEQ ID NO: 2) concentration in test solution | 0.25, 0.5, 1.0, 2.0 mg enzyme protein per liter (ep/l) | |
| Reference enzyme (SEQ ID NO: 12) | 1.0 mg ep/l and 2.0 mg ep/l | |
| Drying | For calculating wash performance Same as for solution A, B and C. For calculating odor: Same as for solution A, B and C. | |
| Test material | Cream turmeric swatch as described below (EMPA221 was used as cotton textile) | |

Cream-turmeric swatches were prepared by mixing 5 g of turmeric (Santa Maria, Denmark) with 100 g cream (38% fat, Arla, Denmark) at 50° C. The mixture was kept at this temperature for about 20 minutes and filtered (50° C.) to remove any un-dissolved particles. The mixture was cooled to 20° C. and woven cotton swatches, EMPA221, were first immersed in the cream-turmeric mixture and then allowed to dry at room temperature over night. The swatches were then frozen until use.

The EMPA swatches were obtained from Eidgenössische Materialprüfungs- und Forschungsanstalt-Testmaterials, Mövenstrasse 12, CH-9015 St. Gallen, Switzerland.

Color measurements were measured on the dried swatches and wash performance calculated as described in example 5. The relative performance score (RP) was calculated against the reference enzyme (SEQ ID NO: 12).

The butyric acid release from the dried swatches was measured using GC in accordance with example 6 and compared to the reference lipase (SEQ ID NO: 12). The Risk Performance Odour, R, of the test lipase enzyme and the reference was calculated Results;

| Test solution A: | RP = 0.8 | R = 0.2 |
|---|---|---|
| Test solution B: | RP = 0.9 | R = 0.9 |
| Test solution C: | RP = 0.5 | R = 0.5 |
| Test solution D: | RP = 0.5 | R = 0.1 |

Example 8

BR—Benefit Risk

The Benefit Risk factor describing the performance compared to the reduced risk for odour smell is thus defined as:

$$BR = RP_{avg}/R$$

A lipase is considered to exhibit improved wash performance and reduced odor, if the BR factor is higher than 1.

Example 9

The Expression and the Characterization of the Lipase of the Present Invention

A standard PCR reaction was run using the plasmid DSM 17467 as template and oligo 300305J7 and 200405j1

```
Oligo 300305j7:
                                   (SEQ ID NO: 16)
gccggcggccgcacaatgcgtcttctccctgccctctc Oligo 200405j1:
                                   (SEQ ID NO: 17)
tcgcggcgcgccctagttagccactgctcctttc
```

The PCR fragment and the Aspergillus expression plasmid pENI2516 (the method for constructing is described in WO2004069872-A1, the disclosures of which are incorporated by reference in their entireties.) were cut with restriction enzyme NotI and AscI, purified from gel and ligated according to the standard procedure known by one skilled in the art. The screening for the plasmid DNA is also within the general knowledge of one skilled in the art.

The resulting plasmid was control-sequenced and named pENI4063. The plasmid was transformed into the filamentous fungi *Aspergillus oryzae* using standard technique (cf. WO2004069872-A1). The resulting transformants were screened for lipase expression using para-nitrophenyl-valerate (PNP-valerate). The lipase hydrolysed the carboxylic ester bond, which released PNP, PNP turned yellow, which was detectable by eye.

The transformant giving the highest yellowness was chosen for further fermentation and subsequent purification of the lipase (see previous examples).

Example 10

The Characterization of the Lipase of the Present Invention

AMSA on Cream/Turmeric swatch was performed in the absence of detergent, but in the presence of 25 mM Glycine buffer with pH7, 8, 9, and 10, respectively, to evaluate the expressed lipases of present invention.

The result showed that the expressed lipase of present invention performs like the reference enzyme (SEQ ID NO: 12) in AMSA on Cream/Turmeric swatch at pH 7. At pH 8, the expressed lipase of the present invention shows wash performance. At pH 9, the expressed lipase of present invention performs like the reference enzyme (SEQ ID NO: 12) and at pH 10 the lipase of the present invention has an RPwash of 0.7 when compared to the reference lipase.

Odour measurement of the lipase of present invention after wash in 25 mM Glycine buffer (pH 9) at 1 ppm (RPwash of about 1) reveals an RPodour of about 2.4 compared to the reference lipase (SEQ ID NO: 12).

Deposit of Biological Material

The lipase of the present invention is a lipase which can be purified from the fungal strain *Nectria* sp. A wild type strain of this species, collected for the applicant by The Institute of Microbiology, Chinese Academy of Science, was found on dead branches of unidentified plant, in Yunnan Province, China in 1999. The inventors have also cloned the gene encoding a lipase of the invention into a strain of *E. coli* harboring strain deposited it under the terms of the Budapest Treaty on 21 Jul. 2005 as DSM 17467. The harboring strain was deposited at Deutsche Sammlung von Mikroorganismen und Zelikulturen GmbH, Mascheroder Weg 1b, D-38124 Braunschweig, Germany by Novozymes (China) Investment Co, Ltd.: China Headquarters; 14 Xinxi Road; Shangdi Zone; Haidian District; 100085 Beijing; China on behalf of the applicant. The deposit was made under the terms of the Budapest Treaty on the International Recognition of the Deposits of Microorganisms for the Purpose of Patent Procedures. The deposit was accorded the following number and date:

| Deposit | Accession Number | Date of Deposit |
|---------|------------------|-----------------|
| DSM | 17467 | 21 Jul. 2005 |

The strain has been deposited under conditions that assure that access to the culture will be available during the pendency of this patent application to one determined by relevant patent authorities to be entitled thereto. The deposit represents a substantially pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. An isolated polypeptide having lipase activity selected from the group consisting of:
   (a) a polypeptide comprising an amino acid sequence having at least 80% sequence identity to the mature polypeptide of SEQ ID NO: 2;
   (b) a polypeptide having an amino acid sequence which has at least 80% sequence identity with amino acids 1 to 315 of SEQ ID NO: 2;
   (c) a polypeptide encoded by a polynucleotide that hybridizes under at least high stringency conditions with (i) the complement of the mature polypeptide coding sequence of SEQ ID NO: 1, or (ii) the complement of the cDNA sequence contained in or the genomic DNA sequence comprising the mature polypeptide coding sequence of SEQ ID NO: 1;
   (d) a polypeptide which is encoded by a polynucleotide which hybridizes under at least high stringency conditions with (i) the complement of nucleotides 41 to 1069 of SEQ ID NO: 1, or (ii) the complement of the cDNA sequence contained in or the genomic DNA sequence comprising nucleotides 41 to 1069 of SEQ ID NO: 1; and
   (e) a polypeptide encoded by a polynucleotide comprising a nucleotide sequence having at least 80% sequence identity to the mature polypeptide coding sequence of SEQ ID NO: 1;
   and wherein the high stringency conditions are defined as prehybridization and hybridization at 42° C. in 5×SSPE, 0.3% SDS, 200 micrograms/mL sheared and denatured salmon sperm DNA and 50% formamide, and washing three times each for 15 minutes using 2×SSC and 0.2% SDS at 65° C.

2. An isolated polypeptide comprising the mature polypeptide of SEQ ID NO: 2; or a fragment thereof having lipase activity.

3. The polypeptide of claim 1 having an amino acid sequence which has at least 85% identity with amino acids 1 to 315 of SEQ ID NO: 2.

4. The polypeptide of claim 1 having an amino acid sequence which has at least 90% identity with amino acids 1 to 315 of SEQ ID NO: 2.

5. The polypeptide of claim 1 having an amino acid sequence which has at least 95% identity with amino acids 1 to 315 of SEQ ID NO: 2.

6. The polypeptide of claim 1 having an amino acid sequence which has at least 97% identity with amino acids 1 to 315 of SEQ ID NO: 2.

7. The polypeptide of claim 1, comprising the amino acids 1 to 315 of SEQ ID NO: 2; or a fragment thereof having lipase activity.

8. The polypeptide of claim 2, which is encoded by a polynucleotide comprising the nucleotide sequence of SEQ ID NO: 1; or a subsequence thereof encoding a fragment having lipase activity.

9. The polypeptide of claim 1, which is encoded by a polynucleotide comprising the mature polypeptide coding sequence of SEQ ID NO: 1.

10. The polypeptide of claim 1, which is encoded by a polynucleotide comprising the nucleotide sequence of SEQ ID NO: 1.

11. The polypeptide of claim 1 in a granulate form.

12. A process for preparing dough or a baked product prepared from the dough, comprising incorporating into the dough the polypeptide of claim 1.

13. A baking composition comprising the polypeptide of claim 1 and a baking ingredient.

14. A composition comprising
   a) the polypeptide of claim 1; and
   b) one or more components selected from the group consisting of leavening agent, milk powder, gluten, emulsifier, granulated fat and an oxidant.

15. The composition of claim 14 which is a dough.

* * * * *

SEQUENCE LISTING

```
<160> NUMBER OF SEQ ID NOS: 25

<210> SEQ ID NO 1
<211> LENGTH: 1219
<212> TYPE: DNA
<213> ORGANISM: Nectria sp.
<220> FEATURE:
<221> NAME/KEY: CDS
<222> LOCATION: (41)..(1069)
<220> FEATURE:
<221> NAME/KEY: sig_peptide
<222> LOCATION: (41)..(124)
<220> FEATURE:
<221> NAME/KEY: mat_peptide
<222> LOCATION: (125)..(1069)

<400> SEQUENCE: 1
acaggacccc tagacttgtg taactctcct gattctcaca atg cgt ctt ctc cct         55
                                              Met Arg Leu Leu Pro
                                                          -25 gcc ctc tcc gtg gtc ggc gtt gcc agc gct gcc tcc atc aag agc tat        103
Ala Leu Ser Val Val Gly Val Ala Ser Ala Ala Ser Ile Lys Ser Tyr
            -20                 -15                 -10 ctt cat gcc ttt gag gag cga gct gtt act gtg acc tcc cag aac ctc        151
Leu His Ala Phe Glu Glu Arg Ala Val Thr Val Thr Ser Gln Asn Leu
         -5                  -1   1                   5 gca aac ttc aag ttc tac gtc cag cat gcc act gcc gcg tac tgt aac        199
Ala Asn Phe Lys Phe Tyr Val Gln His Ala Thr Ala Ala Tyr Cys Asn
 10                  15                  20                  25 tac gac cgc gca gct gga gcc ttg att tca tgc tcg agc aac tgc cca        247
Tyr Asp Arg Ala Ala Gly Ala Leu Ile Ser Cys Ser Ser Asn Cys Pro
                 30                  35                  40
```

| | |
|---|---:|
| agt att gaa agc aat gct gct aag att gtg gga tcc ttc gga ggc gag<br>Ser Ile Glu Ser Asn Ala Ala Lys Ile Val Gly Ser Phe Gly Gly Glu<br>              45                    50                    55 | 295 |
| gat acg ggc att gca ggc tac gtc tca act gac gca act cgc aag gag<br>Asp Thr Gly Ile Ala Gly Tyr Val Ser Thr Asp Ala Thr Arg Lys Glu<br>      60                    65                    70 | 343 |
| att gtc gtc tct atc cgt ggc agt att aac gtc cgc aac tgg atc aca<br>Ile Val Val Ser Ile Arg Gly Ser Ile Asn Val Arg Asn Trp Ile Thr<br>75                    80                    85 | 391 |
| aac ctc gac ttc gtc tgg agt tcc tgc tca gat ctg tcg agc aac tgc<br>Asn Leu Asp Phe Val Trp Ser Ser Cys Ser Asp Leu Ser Ser Asn Cys<br>90                    95                 100          105 | 439 |
| aag gcc cac gct ggc ttc aaa gat gct tgg gat gag atc tcc acc gct<br>Lys Ala His Ala Gly Phe Lys Asp Ala Trp Asp Glu Ile Ser Thr Ala<br>              110                 115               120 | 487 |
| gcc aaa gct gca gtc gtc tcg gcg aag aag gcc aac cca agc tac acc<br>Ala Lys Ala Ala Val Val Ser Ala Lys Lys Ala Asn Pro Ser Tyr Thr<br>         125                 130               135 | 535 |
| atc gtc gcc acg gga cac tcc ctt ggt ggt gct gtt gct acc tta gca<br>Ile Val Ala Thr Gly His Ser Leu Gly Gly Ala Val Ala Thr Leu Ala<br>140                    145                 150 | 583 |
| gct gct tac atc cga gct gct gga tat agt gtc gat ctg tac acg ttc<br>Ala Ala Tyr Ile Arg Ala Ala Gly Tyr Ser Val Asp Leu Tyr Thr Phe<br>      155                 160               165 | 631 |
| ggc tcg cca cgt gta gga aat gac tac ttc gcc aac ttc gtc acc agc<br>Gly Ser Pro Arg Val Gly Asn Asp Tyr Phe Ala Asn Phe Val Thr Ser<br>170                    175                 180               185 | 679 |
| caa gcc gga gct gaa tac cgc gtg aca cac ctc gac gac cct gtt cct<br>Gln Ala Gly Ala Glu Tyr Arg Val Thr His Leu Asp Asp Pro Val Pro<br>              190               195               200 | 727 |
| cgt ctt cca ccc atc ctc ttt ggc tac cgt cat acg tct cct gag tac<br>Arg Leu Pro Pro Ile Leu Phe Gly Tyr Arg His Thr Ser Pro Glu Tyr<br>         205                 210               215 | 775 |
| tgg ctg tca aac gga ggc gct act acg acc tat agt ctg tca gac<br>Trp Leu Ser Asn Gly Gly Ala Thr Thr Thr Thr Tyr Ser Leu Ser Asp<br>220                    225                 230 | 823 |
| atc gtg gta tgc gag ggt atc gcc aac acc gac tgc aat gcc ggc acg<br>Ile Val Val Cys Glu Gly Ile Ala Asn Thr Asp Cys Asn Ala Gly Thr<br>      235               240               245 | 871 |
| ctt ggc ctt gat att att gcc cac ctc ata tac ttc cag gat act tcg<br>Leu Gly Leu Asp Ile Ile Ala His Leu Ile Tyr Phe Gln Asp Thr Ser<br>250                    255                 260               265 | 919 |
| gca tgc aac acc gga ttc acg tgg aag cgc gac acg ttg tcg gat gca<br>Ala Cys Asn Thr Gly Phe Thr Trp Lys Arg Asp Thr Leu Ser Asp Ala<br>         270                 275               280 | 967 |
| gag ctc gag gag atg gtg aac aag tgg gct gag cag gat gtc gaa tac<br>Glu Leu Glu Glu Met Val Asn Lys Trp Ala Glu Gln Asp Val Glu Tyr<br>              285               290               295 | 1015 |
| gtc gcc aat ttg acg acg acc gcg tcg aag cga tgg aaa gga gca gtg<br>Val Ala Asn Leu Thr Thr Thr Ala Ser Lys Arg Trp Lys Gly Ala Val<br>         300                 305               310 | 1063 |
| gct aac tagccatgat atcttgggaa gtttacttct tggaaagcag tggatgaaag<br>Ala Asn<br>315 | 1119 |
| taccttatga tcacattgaa gcaatgaact tacaatgata acgtacataa ataaattgtc | 1179 |
| tcgagagagt caaacgtcta aatgaaaaaa aaaaaaaaaa | 1219 |

<210> SEQ ID NO 2

<211> LENGTH: 343
<212> TYPE: PRT
<213> ORGANISM: Nectria sp.

<400> SEQUENCE: 2

```
Met Arg Leu Leu Pro Ala Leu Ser Val Val Gly Val Ala Ser Ala Ala
        -25                 -20                 -15

Ser Ile Lys Ser Tyr Leu His Ala Phe Glu Glu Arg Ala Val Thr Val
        -10                  -5                  -1   1

Thr Ser Gln Asn Leu Ala Asn Phe Lys Phe Tyr Val Gln His Ala Thr
  5                  10                  15                  20

Ala Ala Tyr Cys Asn Tyr Asp Arg Ala Ala Gly Ala Leu Ile Ser Cys
                 25                  30                  35

Ser Ser Asn Cys Pro Ser Ile Glu Ser Asn Ala Ala Lys Ile Val Gly
             40                  45                  50

Ser Phe Gly Gly Glu Asp Thr Gly Ile Ala Gly Tyr Val Ser Thr Asp
         55                  60                  65

Ala Thr Arg Lys Glu Ile Val Val Ser Ile Arg Gly Ser Ile Asn Val
 70                  75                  80

Arg Asn Trp Ile Thr Asn Leu Asp Phe Val Trp Ser Ser Cys Ser Asp
 85                  90                  95                 100

Leu Ser Ser Asn Cys Lys Ala His Ala Gly Phe Lys Asp Ala Trp Asp
                105                 110                 115

Glu Ile Ser Thr Ala Ala Lys Ala Ala Val Val Ser Ala Lys Lys Ala
            120                 125                 130

Asn Pro Ser Tyr Thr Ile Val Ala Thr Gly His Ser Leu Gly Gly Ala
            135                 140                 145

Val Ala Thr Leu Ala Ala Ala Tyr Ile Arg Ala Ala Gly Tyr Ser Val
        150                 155                 160

Asp Leu Tyr Thr Phe Gly Ser Pro Arg Val Gly Asn Asp Tyr Phe Ala
165                 170                 175                 180

Asn Phe Val Thr Ser Gln Ala Gly Ala Glu Tyr Arg Val Thr His Leu
                185                 190                 195

Asp Asp Pro Val Pro Arg Leu Pro Pro Ile Leu Phe Gly Tyr Arg His
            200                 205                 210

Thr Ser Pro Glu Tyr Trp Leu Ser Asn Gly Gly Ala Thr Thr Thr Thr
            215                 220                 225

Tyr Ser Leu Ser Asp Ile Val Val Cys Glu Gly Ile Ala Asn Thr Asp
            230                 235                 240

Cys Asn Ala Gly Thr Leu Gly Leu Asp Ile Ile Ala His Leu Ile Tyr
245                 250                 255                 260

Phe Gln Asp Thr Ser Ala Cys Asn Thr Gly Phe Thr Trp Lys Arg Asp
                265                 270                 275

Thr Leu Ser Asp Ala Glu Leu Glu Met Val Asn Lys Trp Ala Glu
            280                 285                 290

Gln Asp Val Glu Tyr Val Ala Asn Leu Thr Thr Thr Ala Ser Lys Arg
            295                 300                 305

Trp Lys Gly Ala Val Ala Asn
        310                 315
```

<210> SEQ ID NO 3
<211> LENGTH: 24
<212> TYPE: DNA
<213> ORGANISM: Artificial
<220> FEATURE:
<223> OTHER INFORMATION: Primer-as1

```
<400> SEQUENCE: 3
tccagacgaa gtcgaggttt gtga                                          24

<210> SEQ ID NO 4
<211> LENGTH: 24
<212> TYPE: DNA
<213> ORGANISM: Artificial
<220> FEATURE:
<223> OTHER INFORMATION: Primer-as2

<400> SEQUENCE: 4
tactgccacg gatagagacg acaa                                          24

<210> SEQ ID NO 5
<211> LENGTH: 24
<212> TYPE: DNA
<213> ORGANISM: Artificial
<220> FEATURE:
<223> OTHER INFORMATION: Primer-as3

<400> SEQUENCE: 5
aatgcccgta tcctcgcctc cgaa                                          24

<210> SEQ ID NO 6
<211> LENGTH: 22
<212> TYPE: DNA
<213> ORGANISM: Artificial
<220> FEATURE:
<223> OTHER INFORMATION: Primer-s00

<400> SEQUENCE: 6
aacaggaccc ctagacttgt gt                                            22

<210> SEQ ID NO 7
<211> LENGTH: 20
<212> TYPE: DNA
<213> ORGANISM: Artificial
<220> FEATURE:
<223> OTHER INFORMATION: Primer-s01

<400> SEQUENCE: 7
taactctcct gattctcaca                                               20

<210> SEQ ID NO 8
<211> LENGTH: 17
<212> TYPE: DNA
<213> ORGANISM: Artificial
<220> FEATURE:
<223> OTHER INFORMATION: Primer-n1
<220> FEATURE:
<221> NAME/KEY: misc_feature
<223> OTHER INFORMATION: n is a, c, g or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 8
cadaayytng cnaaytt                                                  17

<210> SEQ ID NO 9
<211> LENGTH: 20
```

```
<212> TYPE: DNA
<213> ORGANISM: Artificial
<220> FEATURE:
<223> OTHER INFORMATION: Primer-n2
<220> FEATURE:
<221> NAME/KEY: misc_feature
<222> LOCATION: (12)..(12)
<223> OTHER INFORMATION: n is a, c, g, or t

<400> SEQUENCE: 9
aayttytayg tncadcaygc                                           20

<210> SEQ ID NO 10
<211> LENGTH: 20
<212> TYPE: DNA
<213> ORGANISM: Artificial
<220> FEATURE:
<223> OTHER INFORMATION: Primer-FDR1

<400> SEQUENCE: 10
aggttggcdg cdccctcaca                                           20

<210> SEQ ID NO 11
<211> LENGTH: 20
<212> TYPE: DNA
<213> ORGANISM: Artificial
<220> FEATURE:
<223> OTHER INFORMATION: Primer-FDR2

<400> SEQUENCE: 11
gwwgtgtgcc dgtatccaaa                                           20

<210> SEQ ID NO 12
<211> LENGTH: 274
<212> TYPE: PRT
<213> ORGANISM: Thermomyces lanuginosus

<400> SEQUENCE: 12
```

Ser Pro Ile Arg Arg Glu Val Ser Gln Asp Leu Phe Asn Gln Phe Asn
1               5                   10                  15

Leu Phe Ala Gln Tyr Ser Ala Ala Tyr Cys Gly Lys Asn Asn Asp
            20                  25                  30

Ala Pro Ala Gly Thr Asn Ile Thr Cys Thr Gly Asn Ala Cys Pro Glu
        35                  40                  45

Val Glu Lys Ala Asp Ala Thr Phe Leu Tyr Ser Phe Glu Asp Ser Gly
    50                  55                  60

Val Gly Asp Val Thr Gly Phe Leu Ala Leu Asp Asn Thr Asn Lys Leu
65                  70                  75                  80

Ile Val Leu Ser Phe Arg Gly Ser Arg Ser Ile Glu Asn Trp Ile Gly
                85                  90                  95

Asn Leu Asn Phe Asp Leu Lys Glu Ile Asn Asp Ile Cys Ser Gly Cys
            100                 105                 110

Arg Gly His Asp Gly Phe Thr Ser Ser Trp Arg Ser Val Ala Asp Thr
        115                 120                 125

Leu Arg Gln Lys Val Glu Asp Ala Val Arg Glu His Pro Asp Tyr Arg
    130                 135                 140

Val Val Phe Thr Gly His Ser Leu Gly Gly Ala Leu Ala Thr Val Ala
145                 150                 155                 160

Gly Ala Asp Leu Arg Gly Asn Gly Tyr Asp Ile Asp Val Phe Ser Tyr
                165                 170                 175

Gly Ala Pro Arg Val Gly Asn Arg Ala Phe Ala Glu Phe Leu Thr Val

-continued

```
                 180                 185                 190
Gln Thr Gly Gly Thr Leu Tyr Arg Ile Thr His Thr Asn Asp Ile Val
        195                 200                 205

Pro Arg Leu Pro Pro Arg Glu Phe Gly Tyr Ser His Ser Pro Glu
    210                 215                 220

Tyr Trp Ile Lys Ser Gly Thr Leu Val Pro Val Arg Arg Asp Ile
225                 230                 235                 240

Val Lys Ile Glu Gly Ile Asp Ala Thr Gly Asn Asn Gln Pro Asn
                245                 250                 255

Ile Pro Asp Ile Pro Ala His Leu Trp Tyr Phe Gly Leu Ile Gly Thr
            260                 265                 270

Cys Leu

<210> SEQ ID NO 13
<211> LENGTH: 12
<212> TYPE: PRT
<213> ORGANISM: Artificial
<220> FEATURE:
<223> OTHER INFORMATION: Synthetic Sequence

<400> SEQUENCE: 13

Ala Cys Met Ser His Thr Trp Gly Glu Arg Asn Leu
1               5                   10

<210> SEQ ID NO 14
<211> LENGTH: 14
<212> TYPE: PRT
<213> ORGANISM: Artificial
<220> FEATURE:
<223> OTHER INFORMATION: Synthetic Sequence

<400> SEQUENCE: 14

His Gly Trp Gly Glu Asp Ala Asn Leu Ala Met Asn Pro Ser
1               5                   10

<210> SEQ ID NO 15
<211> LENGTH: 20
<212> TYPE: PRT
<213> ORGANISM: Nectria sp.

<400> SEQUENCE: 15

Ala Val Thr Val Thr Ser Gln Asn Leu Ala Asn Phe Lys Phe Tyr Val
1               5                   10                  15

Gln His Ala Thr
            20

<210> SEQ ID NO 16
<211> LENGTH: 38
<212> TYPE: DNA
<213> ORGANISM: Artificial
<220> FEATURE:
<223> OTHER INFORMATION: oligo for PCR
<220> FEATURE:
<221> NAME/KEY: misc_feature
<222> LOCATION: (1)..(38)

<400> SEQUENCE: 16
gccggcggcc gcacaatgcg tcttctccct gccctctc                           38

<210> SEQ ID NO 17
<211> LENGTH: 34
<212> TYPE: DNA
<213> ORGANISM: Artificial
```

```
<220> FEATURE:
<223> OTHER INFORMATION: oligo for pcr
<220> FEATURE:
<221> NAME/KEY: misc_feature
<222> LOCATION: (1)..(34)

<400> SEQUENCE: 17
tcgcggcgcg ccctagttag ccactgctcc tttc                              34

<210> SEQ ID NO 18
<211> LENGTH: 10
<212> TYPE: PRT
<213> ORGANISM: Artificial
<220> FEATURE:
<223> OTHER INFORMATION: Hypothetical sequence for alignment example.

<400> SEQUENCE: 18

Ala Cys Met Ser His Thr Trp Gly Glu Arg
1               5                   10

<210> SEQ ID NO 19
<211> LENGTH: 14
<212> TYPE: PRT
<213> ORGANISM: Artificial
<220> FEATURE:
<223> OTHER INFORMATION: Hypothetical sequence for alignment example

<400> SEQUENCE: 19

His Gly Trp Gly Glu Asp Ala Asn Leu Ala Met Asn Pro Ser
1               5                   10

<210> SEQ ID NO 20
<211> LENGTH: 20
<212> TYPE: DNA
<213> ORGANISM: Artificial
<220> FEATURE:
<223> OTHER INFORMATION: AUAP - supplied by 3' RACE kit

<400> SEQUENCE: 20
ggccacgcgt cgactagtac                                              20

<210> SEQ ID NO 21
<211> LENGTH: 5
<212> TYPE: DNA
<213> ORGANISM: Artificial
<220> FEATURE:
<223> OTHER INFORMATION: DW-ACP primer DW-ACP1

<400> SEQUENCE: 21 aggtc                                                               5

<210> SEQ ID NO 22
<211> LENGTH: 5
<212> TYPE: DNA
<213> ORGANISM: Artificial
<220> FEATURE:
<223> OTHER INFORMATION: DW-ACP primer DW-ACP2

<400> SEQUENCE: 22 tggtc                                                               5

<210> SEQ ID NO 23
<211> LENGTH: 5
<212> TYPE: DNA
<213> ORGANISM: Artificial
<220> FEATURE:
<223> OTHER INFORMATION: DW-ACP primer DW-ACP3
```

```
<400> SEQUENCE: 23 gggtc                                                                        5

<210> SEQ ID NO 24
<211> LENGTH: 5
<212> TYPE: DNA
<213> ORGANISM: Artificial
<220> FEATURE:
<223> OTHER INFORMATION: DW-ACP primer DW-ACP4

<400> SEQUENCE: 24 cggtc                                                                        5

<210> SEQ ID NO 25
<211> LENGTH: 21
<212> TYPE: DNA
<213> ORGANISM: Artificial
<220> FEATURE:
<223> OTHER INFORMATION: Universal primer

<400> SEQUENCE: 25
tcacagaagt atgccaagcg a                                                     21
```